United States Patent [19]
Whittaker et al.

[11] Patent Number: 5,792,786
[45] Date of Patent: Aug. 11, 1998

[54] NON-STEROIDAL ANTI-INFLAMMATORY FATTY ACID CONJUGATES AND THEIR THERAPEUTIC USE THEREOF

[75] Inventors: Robert George Whittaker; Veronika Judith Bender; Wayne Gerrard Reilly, all of New South Wales, Australia

[73] Assignee: Commonwealth Scientific and Industrial Research Organisation, Campbell, Australia

[21] Appl. No.: 592,399

[22] PCT Filed: Aug. 2, 1994

[86] PCT No.: PCT/AU94/00440

§ 371 Date: Apr. 12, 1996

§ 102(e) Date: Apr. 12, 1996

[87] PCT Pub. No.: WO95/04030

PCT Pub. Date: Feb. 9, 1995

[30] Foreign Application Priority Data

Aug. 2, 1993 [AU] Australia ............... PM0325

[51] Int. Cl.⁶ ................................ A01N 43/38
[52] U.S. Cl. .................. 514/420; 514/317; 514/375;
514/415; 514/411; 514/427; 514/428; 514/450;
514/532; 514/533; 514/539; 514/545; 514/568;
514/569; 514/886; 514/887; 554/104; 554/110;
554/63; 548/440; 548/486; 548/539; 548/500;
548/578; 546/192; 544/90
[58] Field of Search ................... 554/104, 110,
554/63; 514/317, 375, 415, 411, 420, 427,
428, 450, 532, 533, 539, 545, 568, 569,
884, 887; 548/440, 486, 539, 500, 518;
546/192; 544/90

[56] References Cited

U.S. PATENT DOCUMENTS 3,686,238  8/1972  Zaffaroni .

FOREIGN PATENT DOCUMENTS 871709      2/1979  Belgium .
WO 91/09837 7/1991  WIPO .
WO 93/02706 2/1993  WIPO .

OTHER PUBLICATIONS

Reeve. Vivienne E.. et al: "Lack of Correlation Between Suppression of Contace Hypersensitivity by UV Radiation and Photosiomerization of Epidermal Urocanic Acid in the Hairless Mouse", *Photochemistry and Photobiology*, vol. 60, No. 3, pp. 268–273, 1994.

Whittaker, R.G., et al: "A Gentle Method for Linking Tris to Amino Acids and Peptides", *Peptide Research*, vol. 6, No. 3, 1993.

Kaidrey Kays, H., et al: "The Influence of Corticosteroids and Topical Indomethacin of Sunburn Erythema". *The Journal of Investigative Dermatology*, vol. 66, No. 3, 1976.

Snyder, Diane Sekura: "Cutaneous Effects of Topical Indomethacin, an Inhibitor of Prostaglandin Synthesis, on UV–Damaged Skin", *The Journal of Investigative Dermatology*, vol. 64, pp. 322–325, 1975.

William, Linda P., et al: "Molecular and Channel Forming Characteristics of Gramicidin K's: A Family of Naturally Occurring Acylated Gramicidins", *Biochemistry*, vol. 31, No. 32, 1992.

Bissett, D.L., et al: "Photoprotective Effect of Topical Anti–Flammatory Agents Against Ultraviolet Radiation–Induced Chronic Skin Damage in the Hairless Mouse", pp. 153–158, 1989.

Summers, Terry, Derwent Publications Ltd.

*Primary Examiner*—Gary Geist
*Assistant Examiner*—Deborah D. Carr
*Attorney, Agent, or Firm*—Lowe, Price, LeBlanc & Becker

[57] ABSTRACT

The present invention provides therapeutic conjugates which comprise a therapeutic compound bound to one to three acyl groups derived from fatty acids. The therapeutic compounds are preferably non-steroidal anti-inflammatory agents which include a carboxylic acid group. The compounds involve the use of tromethamine or ethanolamine derivative to link the acyl groups derived from fatty acids to the therapeutic compounds.

55 Claims, 5 Drawing Sheets

NON-STEROIDAL ANTI-INFLAMMATORY FATTY ACID CONJUGATES AND THEIR THERAPEUTIC USE THEREOF

FIELD OF THE INVENTION

The present invention relates to therapeutic conjugates which comprise a therapeutic compound bound to one to three acyl groups derived from fatty acids and to methods involving the use of these compounds. In particular the present invention relates to nonsteroidal anti-inflammatory compounds bound to one to three acyl derivatives of fatty acids.

BACKGROUND OF THE INVENTION

Among the most commonly used therapeutic agents are the nonsteroidal anti-inflammatory drugs. These are typically broken into three major groups:

carboxylic acids, pyrazoles, and oxicams.

Of particular interest in the present invention are the nonsteroidal anti-inflammatory agents which include a carboxylic acid group such as salicylates. Of these nonsteroidal anti-inflammatory drugs the most commonly used compounds are acetylsalicylic acid (aspirin), ibuprofen and indomethacin.

The present inventors have now discovered that the nonsteroidal anti-inflammatory drugs and other therapeutic compounds can be linked to one to three fatty acids. These new compounds are believed to improve the transdermal delivery, transdermal uptake, half-life and/or other modes of delivery of these nonsteroidal anti-inflammatory and other therapeutic agents. Further, it is believed that these novel compounds will aid in the oral, internasal and intraocular delivery of the nonsteroidal anti-inflammatory drugs and other therapeutic agents.

SUMMARY OF THE INVENTION

Accordingly, in a first aspect the present invention consists in a compound of the following formula:

in which

X is a therapeutic compound

Y is absent or is one or two amino acids or a peptide or spacer group

B is H or $CH_2O$—$R_3$; and $R_1$, $R_2$ and $R_3$ are the same or different and are either hydrogen, methyl, ethyl, hydroxyl or an acyl group derived from a fatty acid (saturated or unsaturated) with the proviso that at least one of $R_1$, $R_2$ and $R_3$ is an acyl group derived from a fatty acid.

In a second aspect the present invention consists in a compound of the following formula:

in which X represents a therapeutic compound,

Y is absent or is one or two amino acids or a peptide or spacer group, and $R_4$ is an acyl group derived from a fatty acid.

In a third aspect the present invention consists in a method of prolonging the activity of a nonsteroidal anti-inflammatory compound comprising administering the compound in the form in which X is the nonsteroidal anti-inflammatory compound Y is absent or is one or two amino acids or a peptide or spacer group B is H or $CH_2O$—$R_3$; and $R_1$, $R_2$ and $R_3$ are the same or different and are either hydrogen, methyl, ethyl, hydroxyl or an acyl group derived from a fatty acid with the proviso that at least one of $R_1$, $R_2$ and $R_3$ is an acyl group derived from a fatty acid.

In a fourth aspect the present invention consists in a method of prolonging the activity of a nonsteroidal anti-inflammatory compound comprising administering the compound in the form:

in which X represents the nonsteroidal anti-inflammatory compound

Y is absent or is one or two amino acids or a peptide or spacer group, and $R_4$ is an acyl group derived from a fatty acid.

In a fifth aspect the present invention consists in a method of treating burns comprising administering a compound of the formula:

in which X is ibuprofen

Y is absent or is one or two amino acids or a peptide or spacer group

B is H or $CH_2O$—$R_3$; and $R_1$, $R_2$ and $R_3$ are the same or different and are either hydrogen, methyl, ethyl, hydroxyl or an acyl group derived from a fatty acid with the proviso that at least one of $R_1$, $R_2$ and $R_3$ is an acyl group derived from a fatty acid.

In a sixth aspect the present invention consists in a method of treating burns comprising administering a compound of the formula:

in which

X is ibuprofen

Y is absent or is one or two amino acids or a peptide or spacer group, and $R_4$ is an acyl group derived from a fatty acid.

As will be recognised by persons skilled in the art, the compound of the first aspect of the present invention consists of a therapeutic compound linked, optionally via an amino acid(s) to a tromethamine derivative to which is linked an acyl group derived from a fatty acid(s). Similarly, the compound of the second aspect can be recognised as a therapeutic agent linked, optionally via an amino acid(s) to an ethanolamine derivative to which is linked an acyl group derived from a fatty acid.

DESCRIPTION OF THE PREFERRED EMBODIMENTS

In preferred embodiments of the present invention the therapeutic compound is a nonsteroidal anti-inflammatory compound which preferably includes a carboxylic acid group.

The nonsteroidal anti-inflammatory compound may be selected from a wide range of such known compounds including salicylate, acetylsalicylate, salsalate, diflunisal, fendosal, indomethacin, acemetacin, cinmetacin, sulindac, tolmetin, zomepirac, diclofenac, isoxepac, ibuprofen, flurbiprofen, naproxen, ketoprofen, fenoprofen, benoxaprofen, indoprofen, pirprofen, carprofen, mefenamic acid, flufenamic acid, meclofenamate, niflumic acid, tolfenamic acid, flunixin and clonixin. It is, however, presently preferred that X is selected from the group consisting of acetylsalicylate, salicylate, indomethacin and ibuprofen.

Further examples of nonsteroidal anti-inflammatory compounds are provided in Weissman, Scientific American, January 1991, 58–64, the disclosure of which is incorporated herein by reference.

In yet a further preferred embodiment $R_1$, $R_2$ and $R_3$ are either hydrogen or an acyl group derived from a fatty acid.

It will also be apparent to those skilled in this field that substitutions other than methyl, ethyl and hydroxyl are possible at $R_1$, $R_2$ or $R_3$. The prime requirement is that at least one of $R_1$, $R_2$ or $R_3$ is an acyl group derived from a fatty acid.

In a further preferred embodiment of the first aspect of the present invention, each of $R_1$, $R_2$ and $R_3$ are acyl groups derived from fatty acids, and more particularly, are each the same acyl group. It is presently preferred that the fatty acid has a carbon chain of 3 to 18 carbon atoms, more preferably 10 to 18 carbon atoms, and most preferably 16 carbon atoms. In the same manner it is preferred that $R_4$ is an acyl group derived from a fatty acid having a carbon chain of 3 to 18 carbon atoms, more preferably 10 to 18 carbon atoms, and most preferably 16 carbon atoms.

In a further preferred embodiment of the present invention Y is either absent or is alanine or glycine.

In a further preferred embodiment of the present invention the compound is selected from the group consisting of salicylate-Tris-tripalmitate, salicylate-Tris-dipalmitate, salicylate-Tris-monopalmitate, ibuprofen-alanine-Tris-tripalmitate, ibuprofen-alanine-Tris-dipalmitate, ibuprofen-alanine-Tris-monopalmitate, indomethacin-glycine-Tris-monopalmitate, indomethacin-glycine-Tris-dipalmitate indomethacin-glycine-Tris-tripalmitate, indomethacin-glycine-ethanolamine palmitate, and indomethacin-ethanolamine palmitate.

As stated above the compounds may optionally include a linker. Linkers useful in the present invention are well known and include:

1. Between a compound with a carboxyl group and the amino group of Tris
   a) a linker with an amino group to the compound and a carboxyl group to the Tris such as amino acids and antibiotics
   b) a linker with an amino group to the compound and a sulphonic acid group to the Tris such as 2-aminoethanesulphonic acid (taurine)
   c) a linker with an amino group to the compound and an hydroxyl group to the Tris such as 2-aminoethanol (e.g. via a chloride or bromide intermediate)
   d) a linker with an hydroxyl group to the compound and a carboxyl group to the Tris such as glycolic acid, lactic acid etc
   e) a linker with an hydroxyl group to the compound and a sulphonic acid group to the Tris such as 2-hydroxyethanesulphonic acid (isethonic acid)
   f) a linker with an hydroxyl group to the compound and a reactive halide group to the Tris such as 2-chloroethanol
   g) other examples of potentially suitable linkers between a compound with a reactive carboxyl and the amino group of Tris include the compound families exemplified by p-hydroxybenzaldehyde, 2-chloroacetic acid, 1,2-dibromoethane and ethyleneoxide.

2. Between a compound with an hydroxyl group and the amino group of Tris
   a) a linker with a carboxyl group to the compound and a carboxyl group to the Tris such as dicarboxylic acids via the anhydride e.g. succinic anhydride, maleic anhydride etc.
   b) a linker with a carboxyl group to the compound and an aldehyde group to the Tris such as glyoxylic acid (in the presence of a reducing agent e.g. $NaBH_4$).
   c) a linker with a carboxyl group to the compound and a halide group to the Tris such as chloroacetic acid
   d) a linker with a carboxyl group to the compound and a N=C=O group to the Tris such as ethylisocyanatoacetate.

3. Between a compound with an amine group and the amino group of Tris
   a) a linker with a carboxyl group to the compound and a carboxyl group to the Tris such as dicarboxylic acids via the anhydride e.g. succinic anhydride, maleic anhydride etc.
   b) a linker with a carboxyl group to the compound and an aldehyde group to the Tris such as glyoxylic acid (in the presence of a reducing agent e.g. $NaBH_4$
   c) a linker with a carboxyl group to the compound and a halide group to the Tris such as chloroacetic acid
   d) other examples of potentially suitable linkers between a compound with an amide group and the amino group of Tris include the compound families exemplified by acrolein (in the presence of a reducing agent e.g. $NaBH_4$) and acrylic acid.

4. Between a compound with a thiol group and the amino group of Tris

Examples of potentially suitable linkers between a compound with a thiol group and the amino group of Tris include the compound families exemplified by choroacetic acid and acrolein (in the presence of a reducing agent e.g. $NaBH_4$).

In order that the nature of the present invention may be more clearly understood, preferred forms thereof will now be described with reference to the following examples and Figures.

Chemical Abbreviations used:

ATP1=Alanine-Tris-monopalmitate
ATP2=Alanine-Tris-dipalmitate
ATP3=Alanine-Tris-tripalmitate
$CDCl_3$=Chloroform-d
DCC=Dicyclohexylcarbodiimide,
DCM=Dichloromethane, DCU=Dicyclohexylurea DIEA=Diisopropylethylamine.

DMAP=Dimethylaminopyridine.

DMF=Dimethylformamide,

DMSO-$d_6$=Dimethylsulfoxide-$d_6$,

GTP1=Glycine-Tris-monopalmitate

GTP2=Glycine-Tris-dipalmitate

GTP3=Glycine-Tris-tripalmitate

HOSu=N-Hydroxysuccinimide.

Ibuprofen=α-Methyl-4-(2-methylpropyl)benzene acetic acid

Indomethacin=1-(4-Chlorobenzoyl)-5-methoxy-2-methyl-1H-indole-3-acetic acid

NSAID=Nonsteroidal anti-inflammatory drug

TFA=Trifluoroacetic acid.

THF =Tetrahydrofuran,

Tris=2-Amino-2-hydroxy-methyl-1.3 propanediol.

TSTU=(O-(N-Succinimidyl)-N,N,N'N'-tetramethyl uronium tetrafluoroborate,

Z=Benzyloxycarbonyl

MATERIALS AND METHODS

HIGH PERFORMANCE LIQUID CHROMATOGRAPHY (HPLC)

Analytical HPLC was carried out on Millipore Waters HPLC equipment (Waters Chromatography Division of Millipore, Milford, Mass.), comprising of a 6000A series solvent delivery system with an automated gradient controller and Model 746 Data Module. The separations were performed on a Novapak C18 reverse phase column (100×8 mm). Elution of non fatty acyl derivatives was carried out using a linear gradient from 24 to 80% acetonitrile with 0.1% TFA over 5 min at a flow rate of 2 ml/min (System A) ($R_t^A$). Detection was at 260 nm using a Waters Lambda Max Spectrophotometer, Model 480.

The conjugates were analysed on a C18 column with a linear gradient from 40% water: 50% acetonitrile: 10% THF to 50% acetonitrile: 50% THF containing 0.1% TFA over 5 min at a flow rate of 2 ml/min (System B); ($R_t^B$).

PREPARATIVE HPLC

Separations were carried out on a Millipore Waters DeltaPrep 4000 HPLC using PrepPak$^R$ C4 or C18 reverse phase columns (Prep Nova-Pak HR 40×100 mm) eluted with linear gradients using the same eluent buffer systems as for the analytical HPLC at flow rates of 20 ml/min.

NUCLEAR MAGNETIC RESONANCE (NMR)

NMR spectra were recorded with a 200 MHz Bruker spectrometer.

SYNTHESES

Two alternative methods were employed in the syntheses of palmitoyl derivatives of indomethacin and ibuprofen. In one, the active esters of the NSAID compounds were reacted with the freshly prepared, purified GTP1, GTP2, GTP3, or ATP1, ATP2 and ATP3, and in the other, the active esters were reacted with Ala-Tris or Gly-Tris, the products purified and then palmitoylated to give a mixture of mono, di, and tripalmitates. These were then separated and purified as described. Indomethacin-ethanolamide and indomethacin-glycine ethanolamide derivatives were synthesised via the active ester chemistry and palmitoylated.

Preparation of Gly-Tris

The title compound was obtained in quantitative yield by hydrogenation of a solution of Z-Gly-Tris in ethanol at 40 atm. pressure in a Parr hydrogenator in the presence of palladium on carbon (10%). The removal of the benzyloxycarbonyl group was monitored by HPLC (System A). The catalyst was removed by filtration and washed with ethanol. Evaporation of the solvent gave the title product in 95% purity as shown by $^1$H NMR spectroscopy. Ala-Tris was prepared in an analogous manner. The preparation of Z-Gly-Tris and Z-Ala-Tris are described in Whittaker, R. G., Hayes, P. J.,and Bender, V. J. (1993) Peptide Research 6, 125 and Australian Patent No. 649242.

Preparation of Indomethacin-Gly-Tris

To a stirred solution of indomethacin (1 g, 2.80 mmole) in DMF (50 ml), HOSu (484 mg, 4.2 mmole) was added. The solution was cooled to 0° C. and a solution of DCC (618 mg, 3 mmole) in DCM (5 ml) added. Stirring was continued at room temperature for 2 h to give the active ester in 92% yield (HPLC, System A, $R_t$ 8.38 min). DCU was removed by filtration and washed with DCM. The combined filtrates were added to a solution of Gly-Tris (1.70 g, 9 mmole) in DMF (110 ml) and stirring continued at room temperature for 4 h. The title compound was formed in 85% yield as determined by HPLC (System A). The solvents were removed under reduced pressure, and the residual oil extracted with ethyl acetate and dried (MgSO$_4$) to give the title compound as a yellow oil (0.91 g, 61% of the theoretical yield). HPLC (System A) gave a single peak, $R_t$ 5.35.

Preparation of Indomethacin-Gly-Tris Palmitates

To a solution of indomethacin-Gly-Tris (800 mg, 1.48 mmole) in DMF (20 ml), palmitic acid (570 mg, 2.22 mmole) in DCM (20 ml), DCC (310 mg, 1.5 mmole) and DMAP (20 mg) were added at 0° C. with stirring. The reaction was monitored by HPLC (System B). After 16 h under these conditions the indomethacin-Gly-Tris mono, di and tripalmitates were formed in a 66:30:4 ratio. The solvents were evaporated to dryness, the residue redissolved in DCM (100 ml) and washed with water, citric acid (10%), sodium hydrogen carbonate (5%) and water (100 ml each) and dried (MgSO$_4$). Mono, di and tripalmitates were separated by preparative HPLC on a C4 column (System B) to yield products which gave single peaks on analytical HPLC, $R_t$ 7.49, 8.93 and 9.80.$^1$H NMR of all three products indicated however, that some cleavage of the indomethacin molecule occurred during the reaction, most likely due to the effect of aqueous alkali, so an alternative method for these syntheses was employed.

Preparation of GTP1, GTP2 and GTP3

These compounds were obtained by hydrogenation of Z-Gly-Tris-mono, di, and tripalmitates at 40 atm. pressure in a Parr hydrogenator in the presence of palladium on carbon (10%) in ethanol. The removal of the benzyloxycarbonyl group was monitored by HPLC (System B). After removing the catalyst by filtration and evaporation of solvents GTP1, GTP2 and GTP3 were obtained in quantitative yields. The syntheses and purification of Z-GTP1, Z-GTP2, Z-GTP3 and the corresponding alanyl compounds are described in Whittaker, R. G., Hayes, P. J. and Bender, V. J., (1993), Peptide Research 6, 125–128, and Australian Patent No. 649249. The same source describes the synthesis of mono, di, and tri forms of myristate, laurate and caprate.

The following $^1$H NMR data are shown as examples of purity:

1H NMR of GTP2

$^1$HNMR (CDCl$_3$, δ, ppm): 0.87 (6H, t, Palmitate(CH$_3$), J=6.4 Hz), 1.19–1.42 (52H, m, CH$_2$), 1.60 (4H, m, Palmitate (βCH₂), 2.33 (4H, t, Palmitate (α-CH₂), J=7.2 Hz), 3.41 (1H, brs, OH), 3.70 (2H, q, Gly(CH₂), J=7 Hz), 3.80 (2H, s, Tris(CH2)), 4.17 (2H, d, Tris(CH₂), J=10.4 Hz), 4.31 (2H, d, Tris(CH₂), J=11.2 Hz), 7.92 (2H, brs, NH₂).

1H NMR of Z-GTP2

¹HNMR (CDCl₃, δ, ppm): 0.89 (6H, t, Palmitate (CH₃), J=6.4 Hz), 1.19–1.42 (52H, m, CH₂), 1.61 (4H, m, Palmitate (βCH₂)) 2.31 (4H, t, Palmitate (αCH₂), J=7.2 Hz), 3.8 (2H, d, Tris(CH₂), J=5.5 Hz), 3.82 (2H, d, Gly(CH₂), J=8 Hz), 4.21 (2H, d, Tris(CH₂OCO), J=11.6 Hz), 4.39 (2H, d, Tris(CH₂OOCO), J=11.4 Hz), 5.14 (2H, s, Ar–CH₂), 5.31 (1H, t, Glyamide NH), J=5.4 Hz), 6.55 (1H, s, Tris(amide NH), 7.35 (5H, m, Ar (H)).

Production of Indomethacin-Gly-Tris-Dipalmitate

To a solution of indomethacin (716 mg, 2 mmole) in dry DMF (15 ml) TSTU (Fluka, 85972), (1.20 g, 4 mmole) in DMF (10 ml) was added. The apparent pH of the solution was maintained at 8.3 with DIEA and the mixture stirred at room temperature. The formation of the active ester was monitored by reverse phase HPLC on a C18 column (System A). The reaction was complete in 1 h; Rt of indomethacin, 8.08 min; indomethacin-OSu, 8.38 min.

This solution was added dropwise to a solution of Gly-Tris-dipalmitate (GTP2, 640 mg, 1 mmole) in DCM (10 ml). The apparent pH was maintained at 8.3 with DIEA and the reaction monitored by HPLC on a C₁₈ column (System B) After the relative area counts indicated that the reaction had proceeded to 65–70% completion, the solution was evaporated to dryness under reduced pressure.

The title product was obtained in the form of a white solid after chromatography on Silica gel (Kieselgel S. 0.063–0.2 mm, for column chromatography, Riedel-de Haen A. G.) eluting with ethylacetate/hexane (1:9) to (6:4). The fractions were analysed by HPLC (System B). Fractions containing the pure product were combined, evaporated to dryness and lyophilised from tert. butanol.

A solution of a sample of the product in DCM (10 mg/ml) gave a single peak on HPLC, $R^B_t$, 8.89 in higher than 95% purity as demonstrated by ¹H NMR.

¹HNMR (CDCl₃, δ, ppm): 0.86 (6H, t, Palmitate CH₃), J=6.4 Hz), 1.02–1.39 (52H, m, CH₂), 1.59 (4H, m, Palmitate (βCH₂) 2.32 (4H, t, Palmitate (αCH₂), J=7.4 Hz), 2.39 (3H, s, CH₃) 3.69 (2H s, OCH₂) 3.77 (2H, t, Gly(CH₂), J=5.2 Hz), 3.82 (5H, s, Tris(CH₂), OCH₃), 4.19 (2H, d, Tris(CH₂), J=12.2 Hz), 4.37 (2H, d, Tris(CH₂), J=11.6 Hz), 6.23 (1H, t, Glyamide NH), J=5.4 Hz), 6.55 (1H, s, Tris(amide NH) 6.70 (1H, dd, Ar (CH), J=2.4, 8.8 Hz), 6.91 (1H, d, Ar (CH), J=9.1 Hz), 6.93 (1H, d, Ar (CH)J=2.4HZ), 7.49 (2H, d, Ar (CH), J=8.5 Hz), 7.68 (2H, d, Ar (CH), J=8.8 Hz).

Production of Indomethacin-Gly-Tris-Tripalmitate

The title compound was prepared in a manner analogous to that described above for the dipalmitate derivative. Indomethacin (716 mg, 2 mmole), TSTU (1.2 g, 4 mmole) and Gly-Tris-tripalmitate (950 mg, 1 mmole) were reacted and monitored by HPLC (System B). The title compound was obtained after purification on silica gel to give the chromatographically pure compound with a $R_t$ 9.42 (System B).

Preparation of Indomethacin-Glycine

To a suspension of indomethacin (500 mg, 1.40 mmole) in acetonitrile (20 ml), HOSu (177 mg, 1.54 mmole) and DCC (317 mg, 1.54 mmole) were added and the solution stirred at room temperature for 2 h. A solution of glycine (178 mg, 2.38 mmole) and triethylamine (184 mg, 1.82 mmole) in water (10 ml) was added to the resulting indomethacin hydroxysuccinimide ester and stirred for 2 h, diluted with water (60 ml), acidified with 1M HCl and extracted with ethyl acetate (80 ml). After drying (MgSO₄) the solution was evaporated to dryness to give a yellow solid, which was recrystallised from ethylacetate/hexane to give the title product (406 mg, 70% theory) in 95% purity as determined by 1H NMR.

Preparation of Indomethacin-Glycine-Ethanolamide

To a solution of indomethacin-glycine (1.5 g, 3.62 mmole) in acetonitrile/DMF (60 ml, 5:1), HOSu (460 mg, 3.98 mmole) and DCC (820 mg, 3.98 mmole) were added and the solution stirred for 3 h until the reaction was complete. Ethanolamine (445 mg, 7.3 mmole) was added and stirring continued at room temperature for 1 h. Ethylacetate (300 ml) was added and the solution washed with 1M HCl (120 ml) water and with a saturated NaCl solution (120 ml each) and dried (MgSO₄). Evaporation of the solvent gave the crude title product, which on recrystallisation from ethylacetate/hexane afforded the title product (1.45 g, 88% of theory) as a yellow solid.

Preparation of Indomethacin-Glycine-Ethanolamide-Palmitate

To a suspension of indomethacin-glycine-ethanolamide (410 mg, 0.89 mmole) in DCM/DMF (25 ml, 9:1) palmitic acid (240 mg, 0.93 mmole) DMAP (10 mg) and DCC (192 mg, 0.93 mmole), were added and the solution stirred for 16 h. The solution was diluted with DCM (50ml) and washed with 1M HCl, water and saturated NaCl solution (50 ml each) and dried (MgSO₄). After the removal of the solvent, the residue was chromatographed on silica. Elution was with DCM/ethylacetate to afford the title product as a yellow solid. Final purification was by recrystallisation from ethanol (yield 510 mg, 82% of theory).

Preparation of Indomethacin-Ethanolamide

To a solution of indomethacin (1.0 g, 2.80 mmole) in acetonitrile (50ml) HOSu (335 mg, 2.9 mmole) and DCC (605 mg, 2.9 mmole) were added and the solution stirred at room temp. for 1h. Ethanolamine (340 mg, 5.5 mmole) was added and the solution stirred for a further 2 h. DCU was removed by filtration and washed with DCM. The combined filtrates and washes were evaporated and the residue redissolved in DCM (50ml), washed with 1M HCl (30 ml) and water (30 ml) and dried (MgSO₄). Evaporation of the solvent afforded the title compound as a yellow solid (1.1 g, 98% of theory). Recrystallisation from ethyl acetate/hexane with a few drops of DCM afforded the pure product as a light yellow solid (750 mg, 67% theory).

¹HNMR (CDCl₃, δ, ppm) 2.37 (3H, s, CH₃), 2.78 (1H brs, OH), 3.36 (2H, dt, CH₂, J=5.5,5.5 Hz), 3.65 (4H, brs, CH₂CO.CH₂OH), 3.82 (3H, s, OCH₃), 6.16 (1H, brt, amide NH, J=5.5 Hz), 6.68 (1H, dd, Ar(CH), J2.4, 9.1 Hz), 6.87 (1H, d, Ar(CH), J=9.1 Hz), 6.90 (1H, d, Ar(CH), J=2.4 Hz), 7.46 (2H, d, Ar(CH), J=7.9 Hz), 7.64 (2H, d, Ar(CH), J=7.9 Hz).

Preparation of Indomethacin-Ethanolamide-Palmitate

To a solution of indomethacin-ethanolamide (600 mg, 1.50 mmole) in DCM (10 ml) palmitic acid (405 mg, 1.58 mmole), DMAP (10 mg) and DCC (320 mg, 1.55 mmole) were added. The solution was stirred at room temperature for 16 h and diluted with DCM (50ml), washed with 1M HCl (50ml) and water (50 ml) and dried (MgSO₄). On evaporation of the solvent the crude product was obtained as a slightly oily solid, which was then purified by chromatography on silica. Elution was with DCM/ethyl acetate (9:1) to (8:2) to afford the title compound. Recrystallisation from ethyl acetate gave 610 mg, (66% of the theory) as a dense solid.

¹HNMR (CDCl₃, δ, PPm) 0.86 (3H, t, Palmitate (CH₃, J=6.4 Hz), 1.20–1.42 (26H, m), 1.46 (2H, m, Palmitate ($\beta CH_2$)), 2.05 (2H, t, J=7.9 Hz), 2.38 (3H, s, $CH_3$) 3.45 (2H, dt, $CONHCH_2$, J=5.5, 5.5 Hz), 3.63 (2H, s, $CH_2$) 3.80 (3H, s, $OCH_3$), 4.08 (2H, t, $CH_2$—OCO J=5.5 Hz), 5.95 (1H, brt, amide NH, J=5.5 Hz), 6.67 (1H, dd, Ar(CH), J=2.4, 9.1 Hz), 6.84 (1H, d, Ar(CH), J=9.1 Hz), 6.85 (1H, d, Ar(CH), J=2.4 Hz), 7.47 (2H, d, Ar(CH), J=8.5 Hz), 7.70 (2H, d, Ar(CH), J=8.5 Hz).

SYNTHESES OF IBUPROFEN CONJUGATES

Preparation of Ibuprofen-Ala-Tris-Monopalmitate

Ibuprofen (206.3 mg, 1 mmole) in DMF (5 ml) was reacted with TSTU (377 mg, 1.25 mmole) which had been dissolved in DMF (5 ml) at pH 8.5 (DIEA). The formation of ibuprofen-OSu was monitored by HPLC (System A) and was found to be complete in 10 min, $R_t^A$ 5.70.

To this mixture a solution of ATP1 (536 mg, 1.25 mmole) in DCM (10 ml) was added and the pH maintained at 8.5 (DIEA). The formation of the title product was monitored by HPLC (System B). At the completion of the reaction the solvents were evaporated under reduced pressure.

Preparative HPLC on a C4 column gave the chromatographically pure sample, $R_t^B$ 7.83.

Ibuprofen-Ala-Tris-Dipalmitate

The title product was prepared in the manner as described above for the monopalmitate. Ibuprofen-OSu was reacted with ATP2 (835 mg 1.25 mmole) to give the chromatographically pure sample, $R_t^B$ 9.17 min.

Ibuprofen-Ala-Tris-Tripalmitate

The title product was synthesised as above; ibuprofen-OSu was reacted with ATP3 (1.134 g, 1.25 mmole) to give the chromatographically pure sample, $R_t^B$ 10.43.

Molecular weights of ibuprofen palmitates were determined by Mass Spectrometry to give clean peaks for 619.5, 858.0 and 1096.5, in good agreement with the calculated molecular weights. $^1H$ NMR studies of these preparations indicated, however, that the procedure resulted in a racemic mixture, so an alternative method was employed, which involved the separation of isomers by crystallisation of the ibuprofen-Ala-Tris compound.

Preparation of Ibuprofen-Ala-Tris

To a solution of ibuprofen (3 g, 14.5 mmole) in DCM (50 ml), HOSu (2.49 g, 21.6 mmole) and DIEA (1.25 ml, 7.25 mmole) were added and the solution cooled to 0° C. DCC (3 g, 14.5 mmole) dissolved in DCM (20 ml) was dropped into the reaction mixture. It was stirred at 0° C. for 2 h followed by continued stirring at room temperature for 12 h to obtain the activated ester (ibuprofen-OSu) in 95% yield by HPLC. The DCU precipitate was filtered off and Ala-Tris (2.77 g, 14.5 mmole) dissolved in DMF (10 ml) was added to the reaction mixture and stirring continued at room temperature for 4 h. The title compound was formed in 70% yield by HPLC. $R_t^A$: 5.43. The solvents were removed under reduced pressure and the oily residue dissolved in DCM and washed with citric acid (4%), sodium bicarbonate (5%) and water. The DCM was dried (MgSO4) and evaporated to dryness, to obtain 5.4 g of an oily compound. The oily residue was a 50/50 racemized mixture which was identified by its $^1$HNMR spectrum. The doublet peak of methyl proton of alanine and ibuprofen of the diasteroisomers shifted away about 6 Hz from each other.

$^1$HNMR of mixture (CDCl$_3$, $\delta$, ppm): 0.89 (6H, d, Ibu (CH$_3$), J=6.4 Hz), 1.22, 1.25 (3H, 2d, Ala (BCH3), J=5.2 Hz), 1.40, 1.43 (3H, 2d, Ibu (BCH$_3$), J=4.9 Hz), 1.86 (1H, m, Ibu (CH)), 2.46 (2H, d, Ibu (CH$_2$), J=7 Hz), 3.57 (1H, q, Ibu ($\alpha$CH), J=7.9 Hz), 3.67 (6H, s, Tris (CH$_2$), 4.14 (3H, brs, Tris (OH)), 4.28 (1H, m, Ala ($\alpha$CH), 5.99, 6.02 (1H, 2d, Ala amide NH), J=6.7 Hz, 7 Hz), 7.09 (1H, s, Tris-(amide NH), 7.16 (4H, m, Ar (H)).

The two different diasteroisomers were separated successfully by partial crystallisation of the racemate in DCM (1.6 g). Similar work has been also described by M. Bodanszky, "Principles of Peptide Synthesis", volume 16, Springer-Verlag, Berlin 1984. $^1$HNMR of the crystals and the oily residue confirmed the purity of the diasteroisomers.

$^1$HNMR of the crystal (CDCl$_3$, $\delta$, ppm): 0.89 (6H, d, Ibu (CH$_3$), J=6.4 Hz), 1.3 (3H, d, Ala ($\beta$CH$_3$), J=7.6 Hz), 1.48 (3H, d, Ibu (CH$_3$), J=7.3 Hz), 1.86 (1H, m, Ibu (CH)), 2.46 (2H, d, Ibu (CH$_2$), J=7 Hz), 3.57 (1H, q, Ibu ($\alpha$CH), J=7.9 Hz), 3.67 (6H, s, Tris (CH$_2$)), 4.14 (3H, brs, Tris (OH)), 4.28 (1H, m, Ala ($\alpha$CH), 6.02 (1H, d, Ala(amide NH, J=6.4 Hz), 7.09 (1H, s, Tris (amide NH)), 7.16 (4H, m, Ar (H)).

Ibuprofen-Ala-Tris-Palmitates

To a solution of ibuprofen-Ala-Tris (crystalline product, 1.2 g, 3 mmole) in a 50 % dry DCM/DMF solvent mixture (40 ml), palmitic acid (0.924 g, 3.6 mmole) and a catalytic amount of DMAP (20 mg) were added and the reaction mixture cooled to 0° C. DCC (0.77 g, 3.6 mmole) dissolved in DCM (20 ml) was dropped into the reaction mixture. It was stirred at 0° C. for 1 h and at room temperature for 20 h. The ratio of the mono, di, and tripalmitates of ibuprofen was 55%, 39% and 6% by HPLC (System B).

The solvent was evaporated to dryness and the residue was redissolved in DCM, the DCU filtered off and the filtrate washed with sodium bicarbonate (5%) and water. Preparative HPLC of this mixture on a C18 column yielded high purity compounds of monopalmitate (520 mg, Rt$^B$: 7.81 min), dipalmitate (720 mg, Rt$^B$: 9.24 min), and tripalmitate (63 mg, Rt$^B$: 10.29 min) compounds (Total yield: 56%).

$^1$HNMR of the mono palmitate (CDCl$_3$, $\delta$, ppm) : 0.87 (3H, t, palmitate (CH$_3$), J=6.4 Hz) 0.89 (6H, d, Ibu (CH$_3$), J=6.4 Hz), 1.13–1.40 (26H, m, palmitate (CH$_2$)), 1.49 (3H, d, Ibu ($\beta$CH$_3$), J=7 Hz), 1.58 (5H, m, Ala ($\beta$CH$_3$), palmitate ($\beta$CH$_2$)), 1.86 (1H, m, Ibu ($\alpha$CH)), 2.46 (2H, d, Ibu (CH$_2$), J=7 Hz), 3.56 (1H, q, Ibu ($\alpha$CH), J=7 Hz), 3.64 (2H, t, Tris (CH$_2$), J=7.9 Hz), 3.74 (2H, t, Tris(CH$_2$), J=6.1 Hz), 3.82 (1H, t, Tris(OH), J=6.4 Hz), 3.99 (1H, t, Tris(OH), J=6.7 Hz), 4.26 (2H, s, Tris(CH$_2$)), 4.27 (1H, m, Ala($\alpha$CH)), 5.77 (1H, d, Ala amide NH), J=6.7 Hz), 6.87(1H, s, Tris-NH), 7.16 (4H, m Ar(H)).

Preparation of Salicylate-Tris

Methyl salicylate (2.3g, 15, 1mmole) was reacted with Tris (14.8 g, 120.8 mmole) in DMF (182 ml) and water (121 ml) at pH 9.0 and 60° C. for 48 h. The formation of the title product (Rt 3.95) from methyl salicylate (Rt 7.66) was monitored by HPLC (System A) until the reaction stopped at 75% of completion. The mixture was then evaporated to dryness under reduced pressure and the sample dissolved in water. The pH was adjusted to 4.5 and the title product purified by preparative HPLC followed by ion exchange chromatography (Amberlite IR63 resin) to give the chromatographically pure salicylate-Tris (3.66, 65% of theoretical).

The salicylate-Tris is then ready for reaction with one to three fatty acids.

THE ANTI-INFLAMMATORY EFFECT OF MODIFIED NSAID'S AFTER ACUTE UVB INDUCED PHOTODAMAGE IN SKH-1 HAIRLESS MICE

Introduction

Chronic exposure of albino hairless mice (SKH-1) to sub-erythemal doses of ultraviolet (UV) light induces both visible and histological changes in the skin (Bissett et al., 1990). Acute exposure to UVB light induces sunburn erythema and oedema. Both these effects are transient and disappear within a few days (Reeve et al., 1991).

Kaidbey and Kurban, in 1976, and Snyder, 1975, both examined the extent to which topical indomethacin would suppress sunburn erythema in humans and guinea-pigs. In their experiments indomethacin was found to have a profound effect on erythema. The concentration which was found to be most effective was 2.5% indomethacin in a propylene glycol:ethanol:dimethylacetamide vehicle (19:19:2). The subjects received 3 MED's (median erythema doses) of UV light and indomethacin treatment at this concentration gave total protection.

Method

Groups of 3 female mice were exposed to 3 MED of UVB on their dorsal surface and then were immediately painted (by smoothing the topical solution over the dorsal surface) with 60 µl or 100 µl of vehicle or vehicle containing increasing concentrations of NSAID's or NSAID fatty acid conjugates. The vehicle used was a variation of previously published vehicles and consisted of ethanol:DMSO at a 5:1 ratio. The test NSAID's and their conjugates were either applied after UVB irradiation to reduce the possibility of sun-screening effects (Day 0), or 1 to 5 days prior to UVB exposure. The oedema was then determined by measuring the skin fold thickness (SFT) of a folded mid-dorsal piece of skin using a hand-held micrometer. Measurements were taken at 0 hours, just prior to UVB exposure and at 24 hours post UVB exposure. A control group, painted with 60 or 100 µl of the vehicle, was used to determine the increase in skin oedema due to the inflammatory response. The time point of 24 hours was 20 found to have maximal skin oedema. The pre UVB SFT measurement was subtracted from the 24 hour SFT measurement, to determine the Net Skin Fold Thickness increase (NSFT)

BRIEF DESCRIPTION OF THE DRAWINGS

Results

Indomethacin protection against oedema

Figure 1:
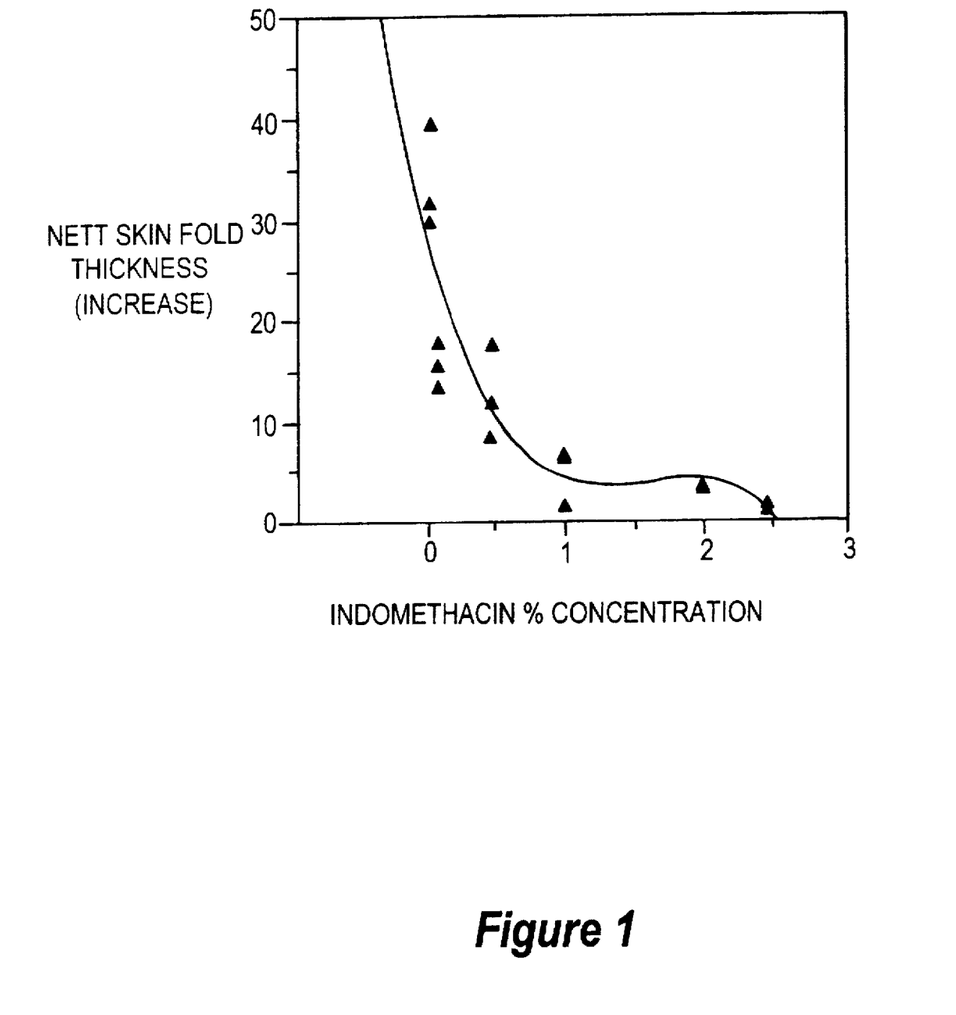

As a preliminary study the ability of indomethacin to protect against oedema in Skh-1 mouse was determined. Indomethacin over a concentration range from 0.1% to 2.5% was applied after the mice had been irradiated with UVB; non-irradiated controls were also run. Initially it was found that at concentrations of 2% and above, the indomethacin was lethal after 36 hours inducing typical gastrointestinal haemorrhage. This led to the setting of 1% indomethacin as the upper concentration in further experiments. Young mice were found to be even more susceptible to gastrointestinal damage and a limit of 0.75% indomethacin was set. NSFT measurements for this experiment are presented in FIG. 1 (▲24 hour indomethacin NSFT).

Mice that had not been exposed to UVB and painted with vehicle or vehicle plus indomethacin showed no sign of erythema or oedema indicating that neither the vehicle, the application method nor the indomethacin induced an inflammatory response. The mice that had been exposed to UBV and treated with indomethacin showed a decrease in erythema and oedema with increasing concentrations of indomethacin. Concentrations of 0.1% indomethacin had a mild anti-inflammatory effect, with maximal protection occurring with 1% indomethacin and above.

Indomethacin-Fatty acyl conjugates results

The indomethacin-fatty acyl conjugates were examined using an unexposed group of Skh-1 female mice. It had been determined previously that the crude indomethacin-fatty acyl conjugates were not protective at concentrations below 1% (w/v based on the indomethacin content) (data not shown). The concentrations tested in the following experiments were 2% (w/v based on the indomethacin content) and were applied to the skin either after exposure to UVB or 5 days, 3 days and 1 day pre UVB exposure.

An aliquot of 100 µl of a 1% (w/u) solution of indomethacin in a 5:1 ethanol:DMSO vehicle was painted onto the dorsal surface of female hairless mice (Skh-1) at time intervals prior to their exposure to UVB, days −5 to −1 and after UVB exposure Day 0. Their NSFT was then calculated at 24 hours post exposure and presented in FIG. 2 (◊ vehicle; ×1% indomethacin). A logarithmic fit of the data indicates that 1% indomethacin loses its protective effect on UVB induced oedema as the interval of application prior to exposure increases.

Figure 2:
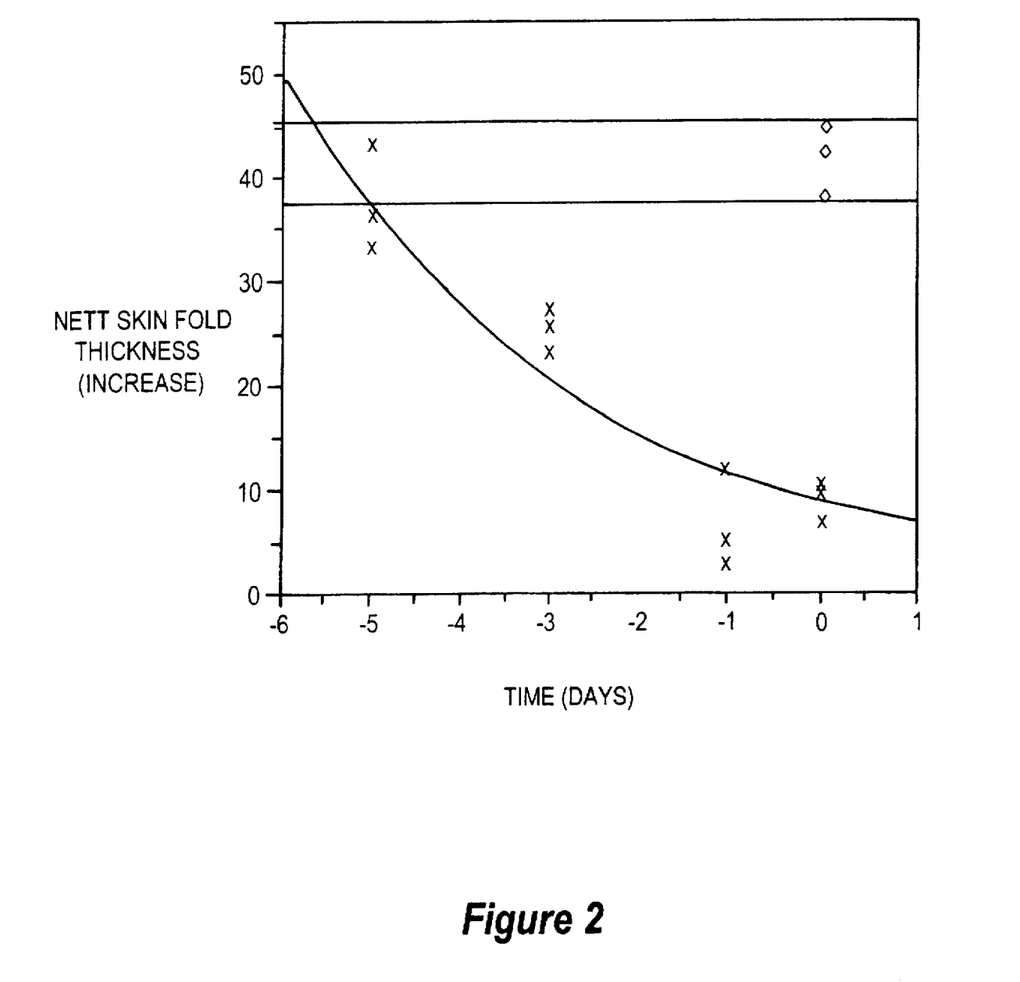
Figure 3:
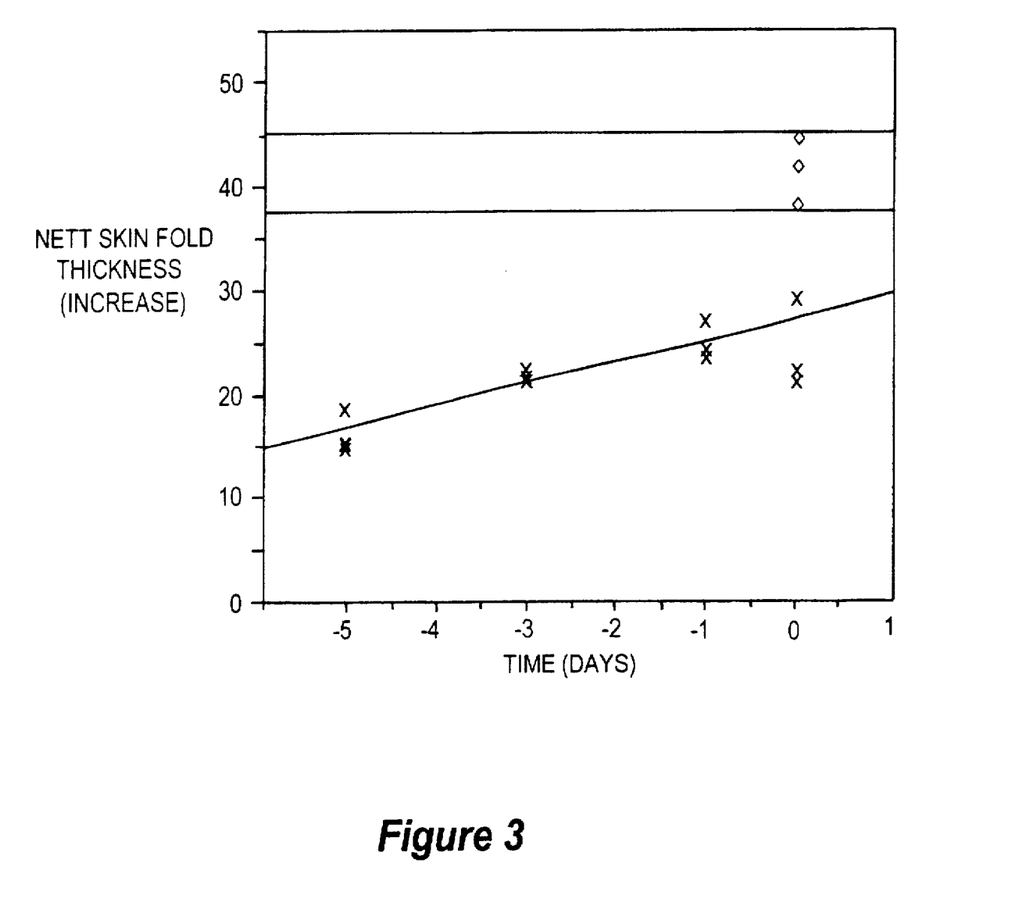

In FIG. 3 groups of Skh-1 mice were painted with 100 µl aliquots of crude 2% indomethacin-glycine-Tris-dipalmitate (30% purity contaminated with GTP2; free of uncoupled indomethacin) at the same time intervals prior to UVB exposure as for free indomethacin in FIG. 2 (◊ vehicle; ×2% indomethacin-GTP2). A linear fit of the data indicates a different profile to that seen with unmodified indomethacin. Photoprotection against UVB induced oedema was most pronounced at 5 days prior to exposure with UVB, indicating that prolonged protection against UVB induced oedema was occurring.

Indomethacin was found to be approximately 50% protective 3 days prior to exposure with UVB, but this protection was not present 5 days prior to exposure, FIG. 2. The Indo-GTP2 was found to be most protective 5 days prior to irradiation with UVB.

Figure 4:
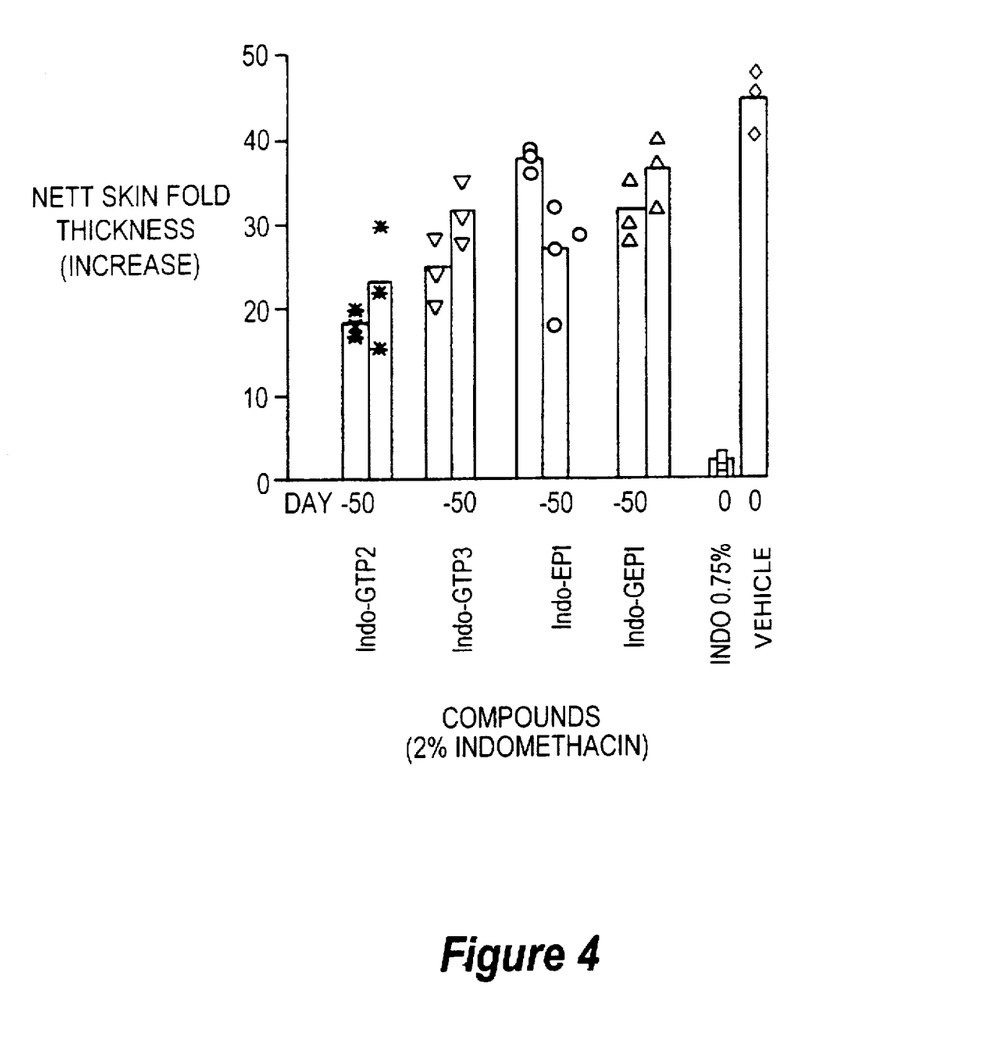

In FIG. 4 groups of 3 mice were painted with 2% solutions (indomethacin equivalent) of high purity indomethacin-glycine-Tris-dipalmitate (Indo-GTP2), indomethacin-glycine-Tris-tripalmitate (Indo-GTP3), indomethacin ethanolamine monopalmitate (Indo-EP1) or indomethacin-glycine-ethanolamine-monopalmitate (Indo-GEP1) and tested for prolonged protective activity by painting 5 days prior to UVB exposure or for immediate activity by painting immediately after UVB exposure; 0 days. The controls were 0.75% indomethacin and vehicle (5:1 ethanol:DMSO). Indomethacin-GTP2 was found to have highest levels of prolonged and immediate activity. This confirmed the finding presented in FIG. 3 for the crude preparation.

Ibuprofen-alanine-Tris-fatty acyl conjugate results

Figure 5:
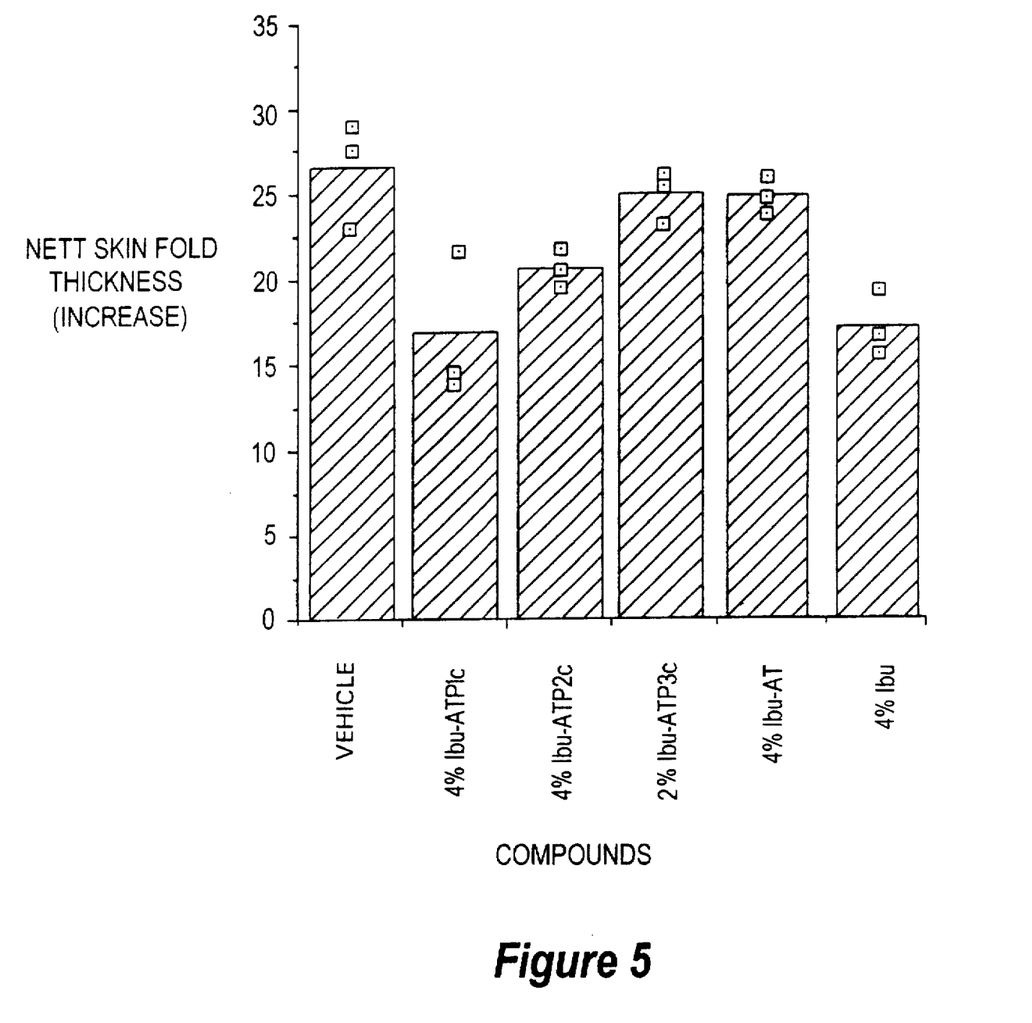

Experiment examining the anti-inflammatory effects of ibuprofen-fatty acyl conjugates have indicated that they are active in protecting against UVB induced oedema. FIG. 5 shows the 2% and 4% results for ibuprofen-fatty acid conjugates.

Groups of 3 mice were exposed to 3 MED of UVB and then painted with 4% (ibuprofen equivalent) solutions of ibuprofen-alanine-Tris-monopalmitate (Ibu-ATP1c), ibuprofen-alanine-Tris-dipalmitate (Ibu-ATP2c), ibuprofen-alanine-Tris-tripalmitate (Ibu-ATP3c, at 2%) or ibuprofen-alanine-Tris (Ibu-AT). The controls were 4% ibuprofen (Ibu) or Vehicle alone.

Immediate Activity Results. - highest to lowest

4% Ibu=4% Ibu-ATP>4% Ibu-ATP2>4% Ibu-AT=2% Ibu-ATP3

(c=crystalline Ibu-alanine-Tris form used in the synthesis.)

Ibuprofen-Tris Fatty Acyl Conjugate Effect on Burns

A subsequent finding with Ibuprofen-fatty acid conjugates was their surprising ability to reduce UVB burns and the results of a series of experiments with ibuprofen-alanine-Tris-monopalmitate are presented in Table 1.

TABLE 1

Effect of Ibuprofen and Ibuprofen-ATP1 on UVB induced burns.

Groups of 3 mice were exposed to 3MED of UVB and then painted with 100 µl aliquots of 2% ibuprofen-alanine-Tris-monopalmitate (Ibu-ATP1). The mice were then compared with 2% Ibuprofen (Ibu cont) or vehicle (Vehicle) controls, over an 8 day period and the results tabulated below. The maximum UVB burn is denoted as 5 and the minimum burn 1. If no burn was present a 0 is used.

|         | Day 5   | Day 6   | Day 7   | Day 8   | Day 11  |
|---------|---------|---------|---------|---------|---------|
|         |         | Expt 1  |         |         |         |
| Vehicle |         |         | 4, 4, 3 |         | 0, 0, 0 |
| Ibu cont |         |         | 4, 3, 2 |         | 0, 0, 0 |
| Ibu ATP1 |         |         | 1, 0, 0 |         | 0, 0, 0 |
|         |         | Expt 2  |         |         |         |
| Vehicle | 5, 5, 5 | 5, 5, 5 | 5, 5, 4 | 5, 4, 3 | 0, 0, 0 |
| Ibu cont | 5, 4, 4 | 5, 5, 4 | 4, 4, 4 | 3, 3, 3 | 0, 0, 0 |
| Ibu ATP1 | 4, 3, 3 | 3, 2, 2 | 1, 0, 0 | 0, 0, 0 | 0, 0, 0 |
|         |         | Expt 3  |         |         |         |
| Vehicle | 5, 5, 5 | 5, 5, 5 | 5, 5, 4 | 5, 4, 3 | 0, 0, 0 |
| Ibu cont | 5, 5, 5 | 5, 5, 5 | 5, 5, 4 | 4, 4, 3 | 0, 0, 0 |
| Ibu ATP1 | 4, 3, 1 | 4, 2, 0 | 2, 1, 0 | 1, 0, 0 | 0, 0, 0 |

Individual scores are presented for each mouse ie a result indicated as 5, 4, 3 is interperated as the first mouse having a severe burn, the second mouse a moderate to severe burn and the third mouse a moderate burn.

The results from these experiments indicate that ibuprofen-alanine-Tris-monopalmitate (Ibu-ATP1) has a protective effect on UVB induced burns to a much greater extent than unmodified ibuprofen. This was seen as an initial reduction in burn response and then a faster resolution of the burn yielding a normal epidermis. This result appears to be independent of oedema reduction as 2% ibuprotein (either as the conjugate or as the free drug) have little effect on oedema at this concentration. In addition indomethacin levels that prevent oedema appear to have little or no effect on burn repair.

Conclusion

NSAID-fatty acid conjugates alter the bioavailability of indomethacin and ibuprofen when applied topically. This change in bioavailability is possibly due to a slow-release property which allows prolonged protection against UVB induced oedema. Ibuprofen-fatty acyl conjugates give enhanced burn protection by speeding burn recovery after acute UVB exposure.

The present inventors have shown that the nonsteroidal anti-inflammatory compound component of the compounds of the present invention retain their activity in the conjugates and that this activity is sustained and prolonged. As it is has been suggested in the scientific literature that nonsteroidal anti-inflammatory compounds may have anti-tumour activity it is believed that the compounds of the present invention may also find application in this area.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Bissett, D. L., Chatterjee, R. and Hannon, D. P., 1990. *Photodermatol Photoimmunol Photomed*, Vol 7:pp153-158.

2. Reeve, V. E., *Personal communication*.
3. Kaidbey, K. H. and Kurban, A. K., 1976. *J. Invest. Dermatol.* 1976, Vol. 66, pp153-156.
4. Snyder, D. S. 1975. *J. Invest. Dermatol.*, Vol 64, pp322-325.

We claim:

1. A method of treating burns comprising administering a compound of the formula:

in which

X is ibuprofen

Y is absent or is one or two amino acids or a peptide or spacer group

B is H or $CH_2O-R_3$; and $R_1$, $R_2$ and $R_3$ are the same or different and are either hydrogen, methyl, ethyl, hydroxyl or an acyl group derived from a fatty acid wherein at least one of $R_1$, $R_2$ and $R_3$ is an acyl group derived from a fatty acid.

2. A method as claimed in claim 1 in which $R_1$, $R_2$, and $R_3$ are either hydrogen or an acyl group derived from a fatty acid.

3. A method as claimed in claim 1 in which each of $R_1$, $R_2$ and $R_3$ are acyl groups derived from fatty acids having a carbon chain of 3 to 18 carbon atoms.

4. A method as claimed in claim 1 in which Y is either absent or is alanine or glycine.

5. A method as claimed in claim 1 in which the compound is ibuprofen-alanine-Tris-monopalmitate.

6. A method as claimed in claim 3 in which the acyl groups are derived from fatty acids having a carbon chain of 10 to 18 carbon atoms.

7. A method as claimed in claim 3 in which the acyl groups are derived from fatty acids having a carbon chain of 16 carbon atoms.

8. A method of treating burns comprising administering a compound of the formula:

in which

X is ibuprofen

Y is absent or is one or two amino acids or a peptide or spacer group, and $R_4$ is an acyl group derived from a fatty acid.

9. A method as claimed in claim 8 in which $R_4$ is an acyl group derived from a fatty acid having a carbon chain of 3 to 18 carbon atoms.

10. A method as claimed in claim 8 in which Y is either absent or is alanine or glycine.

11. A method as claimed in claim 9 in which the acyl group is derived from a fatty acid having a carbon chain of 10 to 18 carbon atoms.

12. A method as claimed in claim 9 in which the acyl group is derived from a fatty acid having a carbon chain of 16 carbon atoms.

13. A method of prolonging the activity of a nonsteroidal anti-inflammatory compound comprising administering the compound in the form in which X is the nonsteroidal anti-inflammatory compound Y is absent or is one or two amino acids or a peptide or spacer group B is H or $CH_2O$—$R_3$; and $R_1$, $R_2$ and $R_3$ are the same or different and are either hydrogen, methyl, ethyl, hydroxyl or an acyl group derived from a fatty acid wherein that at least one of $R_1$, $R_2$ and $R_3$ is an acyl group derived from a fatty acid.

14. A method as claimed in claim 13 in which the nonsteroidal anti-inflammatory compound includes a carboxylic acid group.

15. A method as claimed in claim 13 in which the nonsteroidal anti-inflammatory compound is selected from the group consisting of salicylate, acetylsalicylate, salsalate, diflunisal, fendosal, indomethacin, acemetacin, cinmetacin, sulindac, tolmetin, zomepirac, diclofenac, isoxepac, ibuprofen, flurbiprofen, naproxen, ketoprofen, fenoprofen, benoxaprofen, indoprofen, pirprofen, carprofen, mefenamic acid, flufenamic acid, meclofenamate, niflumic acid, tolfenamic acid, flunixin and clonixin.

16. A method as claimed in claim 15 in which the nonsteroidal anti-inflammatory compound is selected from the group consisting of acetylsalicylate, salicylate, indomethacin and ibuprofen.

17. A method as claimed in claim 13 in which $R_1$, $R_2$ and $R_3$ are either hydrogen or an acyl group derived from a fatty acid.

18. A method as claimed in claim 13 in which each of $R_1$, $R_2$ and $R_3$ are acyl groups derived from fatty acids.

19. A method as claimed in claim 13 in which each of $R_1$, $R_2$ and $R_3$ are acyl groups derived from fatty acids having a carbon chain of 3 to 18 carbon atoms.

20. A method as claimed in claim 13 in which Y is either absent or is alanine or glycine.

21. A method as claimed in claim 13 in which the nonsteroidal anti-inflammatory is indomethacin.

22. A method as claimed in claim 18 in which $R_1$, $R_2$ and $R_3$ are each the same acyl group.

23. A method as claimed in claim 19, in which the acyl groups are derived from fatty acids having a carbon chain of 3 to 18 carbon atoms.

24. A method as claimed in claim 19 in which the acyl groups are derived from fatty acids having a carbon chain of 16 carbon atoms.

25. A method of prolonging the activity of a nonsteroidal anti-inflammatory compound comprising administering the compound in the form:

in which

X represents the nonsteroidal anti-inflammatory compound

Y is absent or is one or two amino acids or a peptide or spacer group, and $R_4$ is an acyl group derived from a fatty acid.

26. A method as claimed in claim 25 in which the nonsteroidal anti-inflammatory compound includes a carboxylic acid group.

27. A method as claimed in claim 25 in which the nonsteroidal anti-inflammatory compound is selected from the group consisting of salicylate, acetylsalicylate, salsalate, diflunisal, fendosal, indomethacin, acemetacin, cinmetacin, sulindac, tolmetin, zomepirac, diclofenac, isoxepac, ibuprofen, flurbiprofen, naproxen, ketoprofen, fenoprofen, benoxaprofen, indoprofen, pirprofen, carprofen, mefenamic acid, flufenamic acid, meclofenamate, niflumic acid, tolfenamic acid, flunixin and clonixin.

28. A method as claimed in claim 27 in which X is selected from the group consisting of acetylsalicylate, salicylate, indomethacin and ibuprofen.

29. A method as claimed in claim 25 in which $R_4$ is an acyl group derived from a fatty acid having a carbon chain of 3 to 18 carbon atoms.

30. A method as claimed in claim 25 in which Y is either absent or is alanine or glycine.

31. A method as claimed in claim 25 in which the nonsteroidal anti-inflammatory compound is indomethacin.

32. A method as claimed in claim 29 in which the acyl group is derived from a fatty acid having a carbon chain of 10 to 18 carbon atoms.

33. A method as claimed in claim 29 in which the acyl group is derived from a fatty acid having a carbon chain of 16 carbon atoms.

34. A method of prolonging the activity of indomethacin comprising administering the indomethacin as indomethacin glycine-Tris-dipalmitate or indomethacin-glycine-Tris-tripalmitate or indomethacin-ethanolamine-palmitate or indomethacin-glycine-ethanolamine-palmitate.

35. A compound of the following formula:

in which

X is a nonsteroidal anti-inflammatory compound

Y is absent or is one or two amino acids or a peptide or spacer group

B is H or $CH_2O$—$R_3$; and $R_1$, $R_2$ and $R_3$ are the same or different and are either hydrogen, methyl, ethyl, hydroxyl or an acyl group derived from a fatty acid with the proviso that at least one of $R_1$, $R_2$ and $R_3$ is an acyl group derived from a fatty acid.

36. A compound as claimed in claim 35 in which the nonsteroidal anti-inflammatory compound includes a carboxylic acid group.

37. A compound as claimed in claim 35 in which the nonsteroidal anti-inflammatory compound is selected from the group consisting of salicylate, acetylsalicylate, salsalate, diflunisal, fendosal, indomethacin, acemetacin, cinmetacin, sulindac, tolmetin, zomepirac, diclofenac, isoxepac, ibuprofen, flurbiprofen, naproxen, ketoprofen, fenoprofen, benoxaprofen, indoprofen, pirprofen, carprofen, mefenamic acid, flufenamic acid, meclofenamate, niflumic acid, tolfenamic acid, flunixin and clonixin.

38. A compound as claimed in claim 37 in which X is selected from the group consisting of acetylsalicylate, salicylate, indomethacin and ibuprofen.

39. A compound as claimed in claim 35 in which $R_1$, $R_2$ and $R_3$ are either hydrogen or an acyl group derived from a fatty acid.

40. A compound as claimed in claim 35 in which each of $R_1$, $R_2$ and $R_3$ are acyl groups derived from fatty acids.

41. A compound as claimed in claim 35 in which each of $R_1$, $R_2$ and $R_3$ are acyl groups derived from fatty acids having a carbon chain of 3 to 18 carbon atoms.

42. A compound as claimed in claim 35 in which Y is either absent or is alanine or glycine.

43. A compound as claimed in claim 35 in which the compound is selected from the group consisting of salicylate-Tris-tripalmitate, salicylate-Tris-dipalmitate, salicylate-Tris-monopalmitate, ibuprofen-alanine-Tris-tripalmitate, ibuprofen-alanine-Tris-dipalmitate, ibuprofen-alanine-Tris-monopalmitate, indomethacin-glycine-Tris-monopalmitate, indomethacin-glycine-Tris-dipalmitate indomethacin-glycine-Tris-tripalmitate, indomethacin-glycine-ethanolamine palmitate, and indomethacin-ethanolamine palmitate.

44. A compound as claimed in claim 40 in which $R_1$, $R_2$ and $R_3$ are each the same acyl group.

45. A compound as claimed in claim 41 in which the acyl groups are derived from fatty acids having a carbon chain of 10 to 18 carbon atoms.

46. A compound as claimed in claim 41 in which the acyl groups are derived from fatty acids having a carbon chain of 16 carbon atoms.

47. A compound of the following formula:

in which

X is a nonsteroidal anti-inflammatory compound,

Y is absent or is one or two amino acids or a peptide or spacer group, and $R_4$ is an acyl group derived from a fatty acid.

48. A compound as claimed in claim 47 in which the nonsteroidal anti-inflammatory compound includes a carboxylic acid derivative.

49. A compound as claimed in claim 47 in which the nonsteroidal anti-inflammatory compound is selected from the group consisting of salicylate, acetylsalicylate, salsalate, diflunisal, fendosal, indomethacin, acemetacin, cinmetacin, sulindac, tolmetin, zomepirac, diclofenac, isoxepac, ibuprofen, flurbiprofen, naproxen, ketoprofen, fenoprofen, benoxaprofen, indoprofen, pirprofen, carprofen, mefenamic acid, flufenamic acid, meclofenamate, niflumic acid, tolfenamic acid, flunixin and clonixin.

50. A compound as claimed in claim 47 in which X is selected from the group consisting of acetylsalicylate, salicylate, indomethacin and ibuprofen.

51. A compound as claimed in claim 47 in which each of $R_4$ is an acyl group derived from a fatty acid having a carbon chain of 3 to 18 carbon atoms.

52. A compound as claimed in claim 47 in which Y is either absent or is alanine or glycine.

53. A compound as claimed in claim 47 in which the compound is indomethacin ethanolamine palmitate or indomethacin glycine ethanolamine palmitate.

54. A compound as claimed in claim 51 in which the acyl group is derived from a fatty acid having a carbon chain of 3 to 18 carbon atoms.

55. A compound as claimed in claim 51 in which the acyl group is derived from a fatty acid having 16 carbon atoms.

* * * * *